(12) United States Patent
McDonald (10) Patent No.: US 9,763,963 B2
(45) Date of Patent: *Sep. 19, 2017

(54) TOPICALLY ACTIVE STEROIDS FOR USE IN INTERSTITIAL PULMONARY FIBROSIS

(71) Applicant: Soligenix, Inc., Princeton, NJ (US)

(72) Inventor: George McDonald, Bellevue, WA (US)

(73) Assignee: Soligenix, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/924,454

(22) Filed: Oct. 27, 2015

(65) Prior Publication Data

US 2016/0106760 A1    Apr. 21, 2016

Related U.S. Application Data

(63) Continuation of application No. 12/864,089, filed as application No. PCT/US2009/032015 on Jan. 26, 2009, now Pat. No. 9,168,263.

(60) Provisional application No. 61/023,266, filed on Jan. 24, 2008.

(51) Int. Cl.
| | |
|---|---|
| *A61K 31/00* | (2006.01) |
| *A61K 31/573* | (2006.01) |
| *A61K 9/00* | (2006.01) |
| *A61K 9/28* | (2006.01) |

(52) U.S. Cl.
CPC ............ *A61K 31/573* (2013.01); *A61K 31/00* (2013.01); *A61K 9/0053* (2013.01); *A61K 9/2833* (2013.01)

(58) Field of Classification Search
CPC ...................................... A61K 31/00
See application file for complete search history.

(56) References Cited

U.S. PATENT DOCUMENTS

| | | | | |
|---|---|---|---|---|
| 5,049,389 | A | * | 9/1991 | Radhakrishnan .... A61K 9/0078 264/4.1 |
| 6,096,731 | A | * | 8/2000 | McDonald ........... A61K 31/565 428/451 |
| 2001/0036938 | A1 | | 11/2001 | McDonald |
| 2007/0010502 | A1 | | 1/2007 | Keith et al. |
| 2007/0142435 | A1 | | 6/2007 | Gao et al. |

OTHER PUBLICATIONS

Daley-Yates et al., "Beclomethasone dipropionate: absolute bioavailability, pharmacokinetics and metabolism following intervenous, oral, intranasal and inhaled administration in man," Br J Clin Pharmacol (2001) 51:400-409.

* cited by examiner

*Primary Examiner* — Benjamin Packard
(74) *Attorney, Agent, or Firm* — Lewis Kohn & Walker LLP; David M. Kohn; Kari Moyer-Henry (57) ABSTRACT

The present invention features methods of delivering corticosteroids or metabolites thereof for treating inflammatory conditions otherwise difficult to cure with topical administration.

9 Claims, 2 Drawing Sheets

TOPICALLY ACTIVE STEROIDS FOR USE IN INTERSTITIAL PULMONARY FIBROSIS

RELATED APPLICATIONS

This application is a continuation of U.S. patent application Ser. No. 12/864,089, filed Jul. 22, 2010, now U.S. Pat. No. 9,168,263, claim priority from United States National Stage Application claiming priority under 35 U.S.C. 371 from International Patent Application No. PCT/US09/32015 filed on Jan. 26, 2009, which claims the benefit of priority from U.S. Provisional Application No. 61/023,566, filed on Jan. 24, 2008, the entire contents of which are herein incorporated by reference.

TECHNICAL FIELD OF THE INVENTION

This invention relates to the field of interstitial lung diseases and treatments related thereto.

BACKGROUND OF THE INVENTION

Interstitial Lung Disease (ILD) is a general term that includes a variety of chronic lung disorders. When a person has ILD, the lung is affected in three ways. First, the lung tissue is damaged in some known or unknown way. Second, the walls of the air sacs in the lung become inflamed. Finally, scarring (or fibrosis) begins in the interstitium (or tissue between the air sacs), and the lung becomes stiff.

Breathlessness during exercise can be one of the first symptoms of these diseases. A dry cough also may be present. These are common symptoms that many people ignore. Someone with these symptoms may wait until they feel quite ill before going to the doctor. People with different types of ILD may have the same kind of symptoms but their symptoms may vary in severity. Their chest X-rays may look alike. Further testing is usually recommended to identify the specific type of ILD a person has. Some ILDs have known causes and some (idiopathic) have unknown causes.

ILD is named after the interstitium because this is the tissue affected by fibrosis (scarring). ILD is sometimes also known as "interstitial pulmonary fibrosis." The terms interstitial lung disease, pulmonary fibrosis and interstitial pulmonary fibrosis are often used to describe the same condition and will be used interchangeably herein.

The course of these diseases is unpredictable. If they progress, the lung tissue thickens and becomes stiff. The work of breathing then becomes more difficult and demanding. Some of the diseases improve with medication if treated when inflammation occurs. Some people may need oxygen therapy as part of their treatment. The diseases may run a gradual course or a rapid course. People with ILD may notice variations in symptoms—from very mild to moderate to very severe. Their condition may remain the same for long periods of time or it may change quickly.

While the progress and symptoms of these diseases may vary from person to person, there is one common link between the many forms of ILD. They all begin with an inflammation. The inflammation may affect different parts of the lung, including the following: the walls of the bronchioles (bronchiolitis); the walls and air spaces of the alveoli (alveolitis); the small blood vessels (vasculitis).

Inflammation of these parts of the lung may heal or may lead to permanent scarring of the lung tissue. When scarring of the lung tissue takes place, the condition is called pulmonary fibrosis.

Fibrosis, or scarring of the lung tissue, results in permanent loss of that tissue's ability to transport oxygen. The level of disability that a person experiences depends on the amount of scarring of the tissue. This is because the air sacs, as well as the lung tissue between and surrounding the air sacs, and the lung capillaries, are destroyed by the formation of scar tissue.

Several causes of pulmonary fibrosis are known, including the following:

Infections: These include viral infections such as cytomegalovirus (a particular problem for people with compromised immune systems); bacterial infections, including pneumonia; fungal infections such as histoplasmosis; and parasitic infections.

Occupation and environmental factors: Long-term exposure to a number of toxins or pollutants can lead to serious lung damage. Workers who routinely inhale silica dust (silicosis), asbestos fibers (asbestosis) or hard metal dust are especially at risk of debilitating lung disease. So are people exposed to certain chemical fumes—sulfuric acid, for example—and ammonia or chlorine gases. But chronic exposure to a wide range of substances, many of them organic, also can damage your lungs. Among these are grain dust, sugar cane, and bird and animal droppings. Other substances, such as moldy hay, can be a problem when they cause a hypersensitivity reaction in the lungs (hypersensitivity pneumonitis). Even bacterial or fungal overgrowth in poorly maintained humidifiers and hot tubs can cause lung damage.

Radiation: A small percentage of people who receive radiation therapy for lung or breast cancer show signs of lung damage months (or sometimes years) after the initial treatment. The severity of the damage depends on how much of the lung is exposed to radiation, the total amount of radiation administered, whether chemotherapy also is used and the presence of underlying lung disease.

Drugs: Nearly 50 drugs can damage the interstitium of the lungs, especially chemotherapy drugs, medications used to treat heart arrhythmias and other cardiovascular problems, certain psychiatric medications, and some antibiotics.

Other medical conditions: ILD can occur with other disorders. Often, those conditions don't directly attack the lungs, but instead involve systemic processes that affect tissue throughout the body. Among these are connective tissue disorders and hematological diseases, including systemic lupus erythematosis, rheumatoid arthritis, dermatomyositis, polymyositis, Sjogren's syndrome and sarcoidoisis.

Idiopathic pulmonary fibrosis: Although doctors can determine why some people develop ILD, in most cases the cause isn't known. Disorders without a known cause are considered a subset of ILD and are grouped together under the label idiopathic pulmonary fibrosis or idiopathic ILD. Although the idiopathic diseases have certain features in common, each also has unique characteristics.

Usual interstitial pneumonitis is the most prevalent of the idiopathic ILDs. Accounting for more than half of all cases, it's so common that the terms "usual interstitial pneumonitis" and "idiopathic pulmonary fibrosis" are often used interchangeably. Because usual interstitial pneumonitis develops in patches, some areas of the lungs are normal, others are inflamed and still others are marked by scar tissue. The disease affects twice as many men as women and usually develops between the ages of 40 and 70.

Although the names are nearly identical, pneumonitis is not the same as pneumonia. Pneumonitis is lung inflammation without infection, whereas pneumonia is lung inflammation that results from infection. In addition, pneumonia is generally limited to one or two areas of the lungs, but pneumonitis involves all five lobes—two in the left lung and three in the right.

Other, less common types of idiopathic pulmonary fibrosis include nonspecific interstitial pneumonitis, bronchiolitis obliterans with organizing pneumonia (BOOP), respiratory bronchiolitis-associated ILD, desquamative interstitial pneumonitis, lymphocytic interstitial pneumonitis, acute interstitial pneumonitis and bronchopulmonary dysplasia.

Shortness of breath is the main symptom of idiopathic pulmonary fibrosis. Since this is a symptom of many types of lung disease, making the correct diagnosis may be difficult. The shortness of breath may first appear during exercise. The condition then may progress to the point where any exertion is impossible.

Other symptoms may include a dry cough (without sputum). When the disease is severe and prolonged, heart failure with swelling of the legs may occur.

A very careful patient history is an important tool for diagnosis of idiopathic pulmonary fibrosis. The history will include environmental and occupational factors, hobbies, legal and illegal drug use, arthritis, and risk factors for diseases that affect the immune system. A physical examination, chest X-ray, pulmonary function tests, and blood tests are important.

Bronchoalveolar lavage (BAL), a test which permits removal and examination of cells from the lower respiratory tract, may be used to diagnose idiopathic pulmonary fibrosis. This test helps identify inflammation in lung tissue, and also helps exclude infections and malignancies (cancer) as a cause of a patient's symptoms. The test is done during bronchoscopy, a special examination of the lung.

A lung biopsy can also be performed, either during bronchoscopy or as a surgical procedure that removes a sample of lung tissue for your doctor to study. This procedure is usually required for diagnosis of idiopathic pulmonary fibrosis.

Other diagnostic tests for idiopathic pulmonary fibrosis include: blood tests, pulmonary function tests, chest x-ray and CT scan, to name a few.

There are several different treatment regimens for use in ILD and the related conditions, including the following:

Lung transplantation: This may be an option for younger people with severe forms of ILD who aren't likely to benefit from other treatment options. In order to be considered for a transplant, you must agree to quit smoking if you smoke, be healthy enough to undergo surgery and post-transplant treatments, be willing and able to follow the medical program outlined by the rehabilitation and transplant team, and have the patience and emotional strength and support to undergo the wait for a donor organ. The last is particularly important because donor organs are in short supply. In general, single-lung transplants are more successful in people with ILD than double-lung transplants are. And although many people who receive lung transplants enjoy a good quality of life, the survival rate is lower than it is for other types of transplants. Additionally, there is a quality of life issue with respect to the increased susceptibility to infection, high blood pressure, diabetes and cancer due to the life-long administration of the anti-rejection drugs.

Oxygen therapy: Although oxygen cannot stop lung damage, it can make breathing and exercise easier, prevent or lessen complications from low blood oxygen levels, and improve sleep and sense of well-being for afflicted patients. It can also reduce blood pressure on the right side of the heart. Children with ILD are especially likely to need oxygen therapy.

Cytotoxic drugs: Azathioprine, which is normally used to prevent organ rejection after a transplant, and the anti-cancer drug cyclophosphamide may be used to treat ILD by suppressing inflammation. The drugs are prescribed when corticosteroids fail to improve symptoms or, increasingly, as a first-line treatment in combination with coritcosteroids. Cytotoxic drugs can cause severe side effects, including reduced production of red blood cells, skin cancer and lymphoma.

Antifibrotics: These drugs are used to help reduce the development of scar tissue. In clinical studies, these drugs have shown promise for slowing the progression of lung damage without suppressing the immune system, but real-world results have been disappointing.

Systemic corticosteroid drugs: Although systemic anti-inflammatory drugs, such as prednisone or methyl prednisolone, are the initial treatment of choice, they help only about one in five people with ILD. Those most likely to benefit have a non-idiopathic disorder and reversible changes in their lungs. Systemic corticosteroids seldom improve lung function in people with idiopathic pulmonary fibrosis. If benefits are shown, they are usually temporary in nature. In general, corticosteroid administration lasts for several months until symptoms improve, at which point the administration is tapered. Upon return of the symptoms, further steroid therapy or an immunosuppressive drug such as azathioprine may be recommended. Taken for long periods of time or in large doses, systemic corticosteroids can cause a number of side effects, including glaucoma, bone lose, high blood sugar levels leading to diabetes, poor wound healing and increased susceptibility to infection. Corticosteroids may be administered to treat the inflammation present in some people with IPF. The success of this treatment for many forms of pulmonary fibrosis is variable and is still being researched. Other drugs are occasionally added when it is clear that the corticosteroids are not effective in reversing the disease. Some doctors may use corticosteroids in combination with other drugs when the diagnosis is first established. Which drug treatment plan is effective and how long to use the drugs is the focus of current research.

Pulmonary complications after allogeneic hematopoietic cell transplantation (HCT) remain a major cause of morbidity and mortality. Among the estimated 50,000 to 60,000 hematopoietic cell transplantations performed each year (www.ibmtr.org), approximately 30% to 60% of the transplant recipients will experience a pulmonary complication (Cordonnier C et al., *Cancer*, 1986; 58:1047-1054; Jules-Elysee K et al., *Am Rev Respir, Die* 1992; 146:485-491. A need exists in the field to develop a therapeutic alternative to combat the progression of ILD and the related conditions.

SUMMARY OF THE INVENTION

The present invention provides a novel approach for treating ILD by administering an oral dosage form of beclomethasone dipropionate (BDP) and exposing the pulmonary circulation to a metabolite of BDP, the metabolite being 17-beclomethasone monopropionate (17-BMP).

In one aspect, the present invention provides a method for delivering a corticosteroid or a metabolite thereof to a subject's pulmonary artery by administering to the subject an oral dosage of the corticosteroid. In one embodiment, the corticosteroid is BDP and the metabolite is 17-BMP. Alternatively, the present invention includes any corticosteroid administration used for the alleviation of inflammatory systems, as well as its metabolite.

In another aspect, the present invention provides a pharmaceutical composition for treating damage resulting from ILD comprising 17-BMP.

In another aspect, the present invention provides a method for preventing, ameliorating and/or treating damage resulting from ILD, the method comprising delivering to a subject's pulmonary artery a metabolite of an orally administered corticosteroid.

In yet another aspect, this invention provides methods which increase the delivery of medicaments to lung tissue.

The present invention is based on the discovery that topically active corticosteroids administered orally resulted in a 4-8 fold increase in the quantity of active drug delivered to the lungs over the amount of active drug delivered via an inhalation route. Side effects usually attributed to systemic corticosteroids are therefore minimized by delivery of active drug to the pulmonary artery and by rapid clearance of such drug from the systemic circulation, while controlling the tissue inflammation within the lung.

DETAILED DESCRIPTION OF THE INVENTION

Definitions

The term "an effective amount" as used herein refers to a quantity of topically active corticosteroid which will, upon single or multiple dose oral administration to the patient, be effective in the prophylaxis, amelioration and/or treatment of damage to the structures of the lung caused by or related to inflammation.

The term "preventing, ameliorating and/or treating" as used herein refers to a reduction or elimination of subsequent damage compared with the damage which would have occurred if the oral corticosteroid were not administered; and in the case where the oral corticosteroid is administered after the damage has occurred, a reduction or elimination of such damage.

The term "damage" as used herein refers to any alteration in normal structure or function.

By "lining" is meant any biological material which covers a surface or lines a cavity or the like and which performs protective, screening and/or other functions.

By "topically active" or "locally active", is meant the compound has its principal pharmacological action through tissue near the site where the drug is present. In the case of a topically active corticosteroid (TAC), there is limited systemic exposure either by limited absorption, first pass metabolism by the liver and/or gut, enterohepatic recirculation, protein binding, or rapid elimination from the systemic circulation, and any combination thereof.

By "systemic circulation" it is meant that portion of the circulation which is anatomically distal to the pulmonary circulation, or the circulation resulting from left ventricular outflow into the aorta, arteries, arterioles, capillaries, and venous system, in which a steady-state level of the drug in the circulation has been achieved.

By a "pharmaceutically acceptable carrier or excipient" is meant a carrier or excipient which is compatible with the other ingredients of the composition and not injurious to the patient.

The term "effective amount" means that amount of a drug or pharmaceutical agent that will elicit the biological or medical response of a tissue, system, animal or human that is being sought by a researcher or clinician.

The term "therapeutically effective amount" means any amount which, as compared to a corresponding subject who has not received such amount, results in improved treatment, healing, prevention, or amelioration of a disease or disorder, or a decrease in the rate of advancement of a disease or disorder, and also includes amounts effective to enhance normal physiological function.

The TACs described in the practice of the present invention can be administered in buccal and sublingual dosage forms as tablets, capsules (each including timed release and sustained release formulations), pills, powders, granules, elixirs, tinctures, suspensions, syrups and emulsions.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician can readily determine and prescribe the effective amount of the drug required to combat the enteritis and/or mucositis condition.

Oral dosages in the practice of the present invention, when used for the indicated effects, will range between about 0.01 to about 100 mg/kg of body weight per day of TAC, and particularly about 0.1 to 10 mg/kg of body weight per day. Oral dosage units will generally be administered in the range of from 0.1 to about 250 mg and more preferably from about 1 to about 16 mg. The daily dosage or a 70 kg human will range from 1 mg to 16 mg.

The dosing scheme of the present invention is predicated on the notion that none of the parent TAC delivered (ie. BDP) can be found in the systemic circulation, but that 20-40% of the metabolite (ie. 17-BMP) reaches the systemic circulation. It is thus believed that increasing the parent compound dosing will not result in a burden to the systemic circulation, but will increase the active metabolite in the pulmonary circulation.

In the methods of the present invention, the compounds herein described in detail can form the active ingredient and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Powders are prepared by committing the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

In addition to the TAC, acceptable carriers and/or diluents may be employed and are familiar to those skilled in the art. Formulations in the form of pills, capsules, microspheres, granules or tablets may contain, in addition to one or more TACs, diluents, dispersing and surface-active agents, binders and lubricants. One skilled in the art may further formulate the TAC in an appropriate manner, and in accordance with accepted practices, such as those disclosed in Remington's Pharmaceutical Sciences, Gennaro, Ed., Mack Publishing Co., Easton, Pa., 1990 (incorporated herein by reference). Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes and the like. Lubricants used in these dosage forms include sodium oleate, sodium stearate, magnesium stearate, sodium, benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as symp, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds for use according to the present invention can also be administered in the form of liposome delivery, systems, such as small unilamellar vesicles, large unilamellar vesicles and multilamellar vesicles. Liposomes can be formed from a variety of phospholipids, such as cholesterol, stearylamine or phosphatidylcholines.

The compounds may also be co-administered with soluble polymers as excipients or drug carriers. Such polymers can include polyvinyl-pyrrolidone, pyran copolymer, poly-hydroxypropylmethacryl-amidephenol, poly-hydroxyethyl-aspartamidephenol, or poly-ethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservations and emulsifiers can also be added.

The preferred drugs for use in the composition of the present invention is BDP and its metabolite, 17-BMP. However, the invention is not restricted thereto, and relates to any corticosteroid drug which is locally active and delivered as either the parent drug or an active metabolite to the pulmonary artery for effective treatment of inflammatory interstitial lung diseases. Representative TACs include, but are not limited to, beclomethasone 17,21-dipropionate, alclometasone dipropionate, budesonide, 22S budesonide, 22R budesonide, beclomethasone-17-monopropionate, clobetasol propionate, diflorasone diacetate, flunisolide, flurandrenolide, fluticasone propionate, halobetasol propionate, halcinocide, mometasone furoate, and triamcinalone acetonide. Suitable TACs useful in the practice of this invention are any that have the following characteristics: rapid first-pass metabolism in the intestine and liver, low systemic bioavailability, high topical activity, delivery of active drug to the pulmonary artery and rapid excretion (see, e.g., Thiesen et al., Alimentary Pharmacology & Therapeutics 10:487-496, 1996) (incorporated herein by reference).

The preferred drug is BDP, on account of its very high topical anti-inflammatory activity, and generation within the intestinal tract of a potent metabolite (17-BMP) that is delivered to the pulmonary artery. BDP can therefore be used effectively in very small doses, in the compositions of this invention, and will not enter the systemic circulation to any significant extent. Additionally, the metabolite of BDP, 17-BMP, may be accessed through oral administration of the parent compound. Other corticosteroid drugs (such as budesonide) are also of use. BDP is a compound that is available from a number of commercial sources, such as Schering-Plough Corporation (Kenilworth, N.J.) in bulk crystalline form, and has the following structure (i.e., beclomethasone 17,21-dipropionate):

R = OH—CH$_2$—CH$_2$—COO$^-$

Patients receive a therapeutically acceptable amount of a TAC by oral administration. Suitable capsules or pills generally contain from 0.1 mg to 8 mg TAC, and typically about 1 mg TAC, plus optional fillers, such as lactose, and may be coated with a variety of materials, such as cellulose acetate phthalate. Such an amount may be readily determined by one skilled in the art by well-known dose-response investigations, and will generally range from 0.1 mg/day to 8 mg/day, and more typically range from 4 mg/day to 8 mg/day, or higher used in this particular indication.

It will be appreciated that, although specific embodiments of this invention have been described herein for purpose of illustration, various modifications may be made without departing from the spirit and scope of the invention.

BDP is a glucocorticoid that when taken orally is metabolized in the intestinal lumen and mucosa to a significantly more potent glucocorticoid metabolite, 17-BMP. Studies in normal human volunteers have demonstrated that none of the parent compound (BDP) can be found in the systemic circulation, but that 20-40% of the oral drug that reaches the systemic circulation does so as 17-BMP (Daley-Yates et al). 17-BMP is then rapidly cleared from the circulation. The route by which 17-BMP reaches the circulation is as follows: following formation in the intestine, 17-BMP passes through the portal circulation to the liver, then to the hepatic vein, then to the right atrium and right ventricle, then to the pulmonary artery, the pulmonary vein, then the left atrium, left ventricle, and aorta. Exposure of the pulmonary circulation to the highly potent immunosuppressive glucocorticoid, 17-BMP, is the basis for the idea that inflammatory and fibroinflammatory diseases of the lungs, particularly the diseases that involve the interstitium of the lung, might be effectively and safely treated by oral delivery of the glucocorticoid pro-drug BDP. While inhaled BDP is effective in treating reactive airway diseases that have an inflammatory basis, for example, asthma and chronic obstructive pulmonary disease with chronic bronchitis, inhaled formulations of BDP deliver relatively little 17-BMP to the interstitial space, as much of the inhaled drug reaches the bronchi, smaller airways, and alveoli.

Prednisone therapy is effective in treatment of reactive airway disease and some types of ILD, but is limited by systemic toxicity. Topically active, inhaled BDP was developed to allow delivery of glucocorticoid to the lung so that the systemic toxicity of prednisone could be avoided.

If a person with a pulmonary disorder were given BDP via inhalation, the total daily dose of BDP would be a maximum of 400 .micro.grams (0.4 mg). While there is metabolism of BDP to 17-BMP in the lungs, the maximum daily amount of 17-BMP that reaches the lungs would be limited to 0.4 mg. In contrast, if a daily dose of 8 mg. oral BDP were given, and if 20-40% of that dose was delivered to the pulmonary artery as 17-BMP, the total daily dose of 17-BMP delivered to the lungs would be 1.6 to 3.2 mg, a 4- to 8-fold increase in the amount of drug delivered to the lungs over the inhalation route.

Two multicenter, randomized, placebo-controlled, double-blind trials have been conducted to examine whether oral beclomethasone dipropionate (BDP) is an effective therapy for treatment of gastrointestinal graft-versus-host disease (GVHD) (McDonald G B et al., Gastroenterology, 1998; 115:28-35; Hockenbery D M et al., Blood, 2007; 109:4557-4563). The results of these studies indicate that oral BDP is effective for treating gastrointestinal GVHD, allows rapid taper and less use of systemic corticosteroid therapy, and results in a 45% reduction in mortality risk at one-year post-randomization. In addition to these benefits, the most recent trial revealed that BDP treatment was also associated with fewer cytomegalovirus reactivations (28% versus 39%), fungal infections, (7% versus 14%), and multiple bacteremic episodes (none versus 9%) (Hockenbery D M et al., Blood, 2007; 109:4557-4563).

Of interest to the pulmonary community was the observation that during the 80-day study period, 12/67 (18%) patients on the placebo arm had developed noninfectious pulmonary infiltrative disorders, compared to 0/62 patients in the BDP treatment arm (17). Based upon this initial observation, it was believed that oral BDP may be effective in preserving lung function and preventing the development of early noninfectious pulmonary complications after allogeneic HCT. To test this hypothesis, there was a retrospective review of medical records and a prospective collection of pulmonary function test (PFT) results from all patients who participated in these two randomized trials.

These results represent the first report in the literature of randomized trial data demonstrating a treatment strategy that may be not only protective of lung function after HCT, but useful in the prevention of the almost uniformly fatal noninfectious pulmonary complications that occur in the early post-HCT period. There was a statistically significant preservation of pulmonary diffusing capacity and fewer episodes of non-infectious pulmonary complications in patients randomized to receive oral BDP, compared to placebo. Although the primary objective in each of the two randomized, placebo-controlled trials of oral BDP was not to assess pulmonary outcomes, these findings are consistent with the mortality results of the trials suggesting more favorable outcome in the group randomized to BDP. These trials assessed the ability of this topically active glucocorticoid to control the signs and symptoms of gastrointestinal GVHD while minimizing systemic prednisone exposure. In both trials, the frequency of GVHD treatment failure was significantly reduced at the end of the treatment period and after follow-up among patients randomized to BDP, compared to placebo. These results are also consistent with what is known about the pathophysiology of idiopathic lung injury in the aftermath of allogeneic HCT and the pharmacology of oral BDP and its potent metabolite, 17-BMP.

The reported incidence of IPS in the first 120 days after allogeneic HCT is 3 to 15%, with a lower incidence reported in association with the use of reduced intensity conditioning regimens. Respiratory failure is generally common and usually rapid in onset, with mortality uniformly high, ranging from 60% to greater than 95% for patients requiring mechanical ventilation. Although a few clinical risk factors have been consistently identified in previous studies, including conditioning with total body irradiation, acute GVHD, and older recipient age, accumulating evidence from murine models of lung injury after allogeneic HCT strongly suggest that inflammation plays a significant role in the pathogenesis of IPS. Some of these murine studies have established a causal role for TNF-α in the development of IPS, where administration of a TNF-α binding protein (rhTNFR:Fc) reduces the progression of lung injury during the four to six week period after HCT. Other studies have also suggested that lipopolysaccharide (LPS), which often gains access to systemic circulation early in the post-transplantation period by translocating across gut mucosa damaged by conditioning regimens and acute GVHD, may result in a significant inflammatory cytokine milieu in the lung that results in lung injury (Cooke K R et al., *J Clin Invest*, 1998; 102:1882-1891). Collectively, these data provide strong evidence that overwhelming inflammation within the lungs likely plays a significant role in the pathogenesis of early noninfectious pulmonary complications after HCT. These studies indicate that a sequence of events involving chemokine-driven recruitment of inflammatory and immune-effector cells to the lung, release of oxidants and proinflammatory cytokines, and, in the case of allogeneic transplantation, a second wave of injury mediated by alloreactive T lymphocytes, may lead to the development of IPS.

The formulations of oral BDP used in the randomized trials described here included a gastric-release pill for distribution of BDP to the stomach and upper small intestine, and an enteric-coated pill for distribution to the distal small intestine and colon. Presence of 17-BMP in the blood from the right heart, as demonstrated by our data, suggests that 17-BMP, a product of gastrointestinal mucosal hydrolysis of BDP, was likely absorbed in the gastrointestinal tract and entered the right heart via portal venous circulation. In the HCT situation, we speculate that steady-state delivery of 17-BMP to the pulmonary circulation and ultimately the interstitial space prior to the onset of clinically detectable disease was responsible for reducing pulmonary inflammation, reflected by the preservation of pulmonary diffusing capacity and by the absence of noninfectious pulmonary infiltrates within the first 200 days after randomization.

Consideration of oral BDP as a preemptive agent for these noninfectious pulmonary complications may have several advantages. Although BDP itself is a relatively weak immunosuppressive glucocorticoid, its active metabolite 17-BMP, is a highly potent glucocorticoid. In a human skin vasoconstriction model, where the degree of blanching (vasoconstriction) was interpreted as indicating anti-inflammatory activity, 17-BMP was 3.6-times more potent than triamcinolone-16,17-acetonide, the active ingredient in Azmacort inhalation aerosol (Kos Pharmaceuticals) and 450-times more potent than dexamethasone (Harris D M et al., *J Steroid Biochem*, 1975; 6:711-716).

17-BMP is also much more potent in terms of glucocorticoid receptor-α activity. In competition binding assays, where the affinity value for dexamethasone was arbitrarily set at 100 and affinity values of the other corticosteroids were calculated based on their reduction of specific binding of radiolabeled dexamethasone, 17-BMP's binding affinity was approximately 13-times as potent as dexamethasone (relative binding affinities were BDP: 43, 17-BMP: 1345) (Wurthwein G et al., *Biopharm Drug Dispos*, 1990; 11:381-394). Finally, the relative bioavailability of BDP and its metabolites is much lower in comparison to more commonly used corticosteroids. In a bioavailability study of oral BDP, where BDP was given orally and intravenously to 12 healthy subjects, no BDP was detectable in the plasma following oral administration. However, the total oral bioavailability of the active metabolite 17-BMP was 21-41% (unpublished data). Systemic exposure to 17-BMP is limited by its protein binding and clearance, such that oral BDP 2 mg would give systemic exposure equivalent to a dosing schedule of oral prednisone of 2.5 mg or less than 1 mg of intravenous dexamethasone.

EXAMPLES

Example I: Preservation of Pulmonary Diffusing Capacity with Oral Beclomethasone Dipropionate Patients with biopsy-proven acute gastrointestinal GVHD received an induction course of prednisone (1 mg/kg/day for 10 days) plus either oral BDP pills (8 mg/day in four divided doses, half as a gastric-release formulation and half as an enteric-coated formulation) or placebo. Patients whose symptoms were controlled at study day ten continued on study drug while the prednisone dose was rapidly tapered. Patients whose symptoms required additional prednisone were considered treatment failures. Study drug was discontinued on the day of treatment failure. The duration of treatment with study drug was 30 days with a 10-day follow-up period in the first trial and 50 days with a 30-day follow-up period in the second trial.

Pulmonary Function Testing

Pulmonary function assessments included forced vital capacity (FVC), one-second forced expiratory volume (FEV1), total lung capacity (TLC), and carbon monoxide diffusion capacity ($DL_{CO}$), which was adjusted for hemoglobin level at the time PFTs were obtained. All PFT values were expressed as a percent of the predicted value calculated according to published equations (Crapo R O et al., *Am Rev Respir Dis*, 1981; 123:659-664; Crapo R O et al., *Am Rev Respir Dis*, 1981; 123:185-189). Pretransplantation and Day 80 PFTs were obtained, regardless of the presence or absence of symptoms. After discharge, patients were encouraged to return at one year after transplantation, at which time another PFT was obtained. For purposes of the current study, PFTs performed between days 60 and 100 were considered as valid for the Day 80 PFT and tests performed between days 265 and 465 as valid for the one-year PFT. Change in lung function was assessed by comparing PFT parameters performed prior to start of conditioning to those obtained post-transplantation at Day 80 and one year. Analysis of change in lung function was done on an intent-to-treat basis, by randomization assignment to oral BDP or placebo, with maintenance of the study blind.

Sixty patients had been randomized to oral BDP and the same number to placebo. Serial PFTs at day 80 were available from 44 and 50 patients on placebo and BDP, respectively. Significantly fewer patients randomized to BDP (55%) had deterioration of diffusing capacity by transplant day 80, compared to placebo (79%), $p \leq 0.02$. No such differences were noted in other PFT parameters (see Table 1). In the analysis of change in PFTs from baseline to Day 80, eight patients who did not meet the minimum five-day criterion of treatment with study drug prior to their Day 80 PFT were not included (five in placebo group, three in BDP group). The median time to randomization was 33.5 days after HCT (range, 19-105) for the Phase 2 study and 31 days (range, 16-89) for the Phase 3 study. Several patients were missing baseline, Day 80, or one-year PFT as indicated by the total number of patients contributing to the appropriate analyses summarized Tables 1 and 2. Overall, the majority of the patients had normal pulmonary function prior to transplantation, defined as a percent of the normal predicted value≥80% [FVC 94/114 (82%); FEV1 88/114 (77%); TLC 105/113 (93%); $DL_{CO}$ 84/114 (74%)],

TABLE 1

Proportion of patients whose PFTs decreased from pre-HCT baseline to transplant day 80 and magnitude of changes, by randomization assignment (chi square test).

| PFT parameter | Placebo | BDP | p-value |
|---|---|---|---|
| FEV$_1$ | | | |
| N (%)* | 21/44 (48) | 25/50 (50) | 0.83 |
| Mean change (range) | −1.38 (−25, +19) | −0.05 (−22, +34) | 0.48 |
| FVC | | | |
| N (%)* | 24/44 (55) | 25/50 (50) | 0.66 |
| Mean change (range) | −1.85 (−20, +16) | +0.34 (−30, +35) | 0.26 |
| TLC | | | |
| N (%)* | 25/42 (60) | 29/50 (58) | 0.88 |
| Mean change (range) | −1.67 (−20, +23) | +1.41 (−25, +57) | 0.23 |
| DLCO | | | |
| N (%)* | 33/42 (79%) | 27/49 (55) | 0.02 |
| Mean change (range) | −7.95 (−40, +23) | +0.57 (−74, +115) | 0.08 |

FVC = forced vital capacity,
FEV$_1$ = one second forced expiratory volume,
TLC = total lung capacity,
DLCO = dffusion capacity of carbon monoxide
*N represents proportion of patients who experienced a decrease in that parameter

TABLE 2

Characteristics of BDP and placebo treated patients

| Characteristic | Placebo (N = 60) | BDP (N = 60) |
|---|---|---|
| Median age (range) | 47 (12-66) | 40 (7-67) |
| Recipient:donor sex | | |
| M:M | 17 | 24 |
| M:F | 11 | 12 |
| F:F | 12 | 9 |
| F:M | 20 | 15 |
| Disease | | |
| CML | 13 | 15 |
| AML | 16 | 19 |
| MDS | 17 | 3 |
| ALL | 8 | 8 |
| NHL | 2 | 8 |
| Other | 4 | 7 |
| Donor type | | |
| Unrelated | 24 | 20 |
| Related matched | 31 | 32 |
| Related mismatched | 3 | 7 |
| Conditioning regimen | | |
| TBI-based myeloablative | 28 | 31 |
| Non-TBI-based myeloablative | 28 | 18 |
| Nonmyeloablative | 4 | 11 |
| Randomized study | | |
| Phase II | 29 | 31 |
| Phase III | 31 | 29 |
| Pulmonary function pretransplant * | | |
| FVC (n = 58, 56) | 95.1 | 93.7 |
| FEV$_1$ (n = 58, 56) | 89.9 | 90.4 |
| TLC (n = 57, 56) | 98.6 | 95.7 |
| DLCO (n = 58, 56) | 90.9 | 83.6 |
| Pulmonary function at Day 80 * | | |
| FVC (n = 49, 56) | 93.0 | 93.8 |
| FEV$_1$ (n = 49, 56) | 89.2 | 90.3 |
| TLC (n = 48, 55) | 96.7 | 96.9 |
| DLCO (n = 47, 54) | 81.2 | 86.0 |
| pulmonary function at one year * | | |
| FVC (n = 29, 33) | 94.0 | 89.4 |
| FEV$_1$ (n = 29, 33) | 88.5 | 85.9 |
| TLC (n = 28, 33) | 98.9 | 95.7 |
| DLCO (n = 27, 33) | 74.4 | 78.1 |

M = male;
F = female;
CML = chronic myeloid leukemia;
AML = acute myeloid leukemia;
MDS = myelodysplastic syndrome;
ALL = acutelymphocytic leukemia;
NHL = non-Hodgkins lymphoma;
TBI = total body irradiation,
FVC = forced vital capacity,
FEV$_1$ = one second forced expiratory volume,
TLC = total lung capacity,
DLCO = dffusion capacity of carbon monoxide
* Numbers represent the mean of the percent of predicted normal values Changes in pulmonary function from pre-transplantation to Day 80 after transplantation are summarized in Table 1. The proportion of BDP- and placebo-treated patients who experienced a decrease (of any magnitude) of their pulmonary function from pretransplantation to Day 80 after transplantation was similar for PVC, FEV1, and TLC, with no statistically significant differences. However, there was a statistically significant difference in the proportion of patients who experienced a decrease of the $DL_{CO}$. Among placebo treated patients, 33 of 42 (79%) patients experienced a decrease of the $DL_{CO}$ from pretransplantation to Day 80 after transplantation, compared to 27 of 49 (55%) BDP-treated patients (p=0.02). The mean decrease among placebo-treated patients was 7.95% (range −40% to +23%), while the mean change from baseline to Day 80 was actually increased 0.57% for BDP-treated patients (range −74% to +115%) (p=0.08).

Additional analysis of PFTs obtained at one year after transplantation did not reveal any statistically significant associations of treatment with loss of pulmonary function. However, the decrease from baseline to one year in $DL_{CO}$ was larger in the placebo group compared to the BDP group (placebo: mean decrease of 15.27% among 27 patients with data; BDP: mean decrease of 7.67% among 32 patients with data; p=0.11). In the BDP group, four noninfectious events occurred after Day 200 (FIG. 1; COP/BOOP on Day 207, IPS on Day 212, bronchiolitis obliterans syndrome on Day 244, DAH on Day 269). The COP/BOOP and DAH cases occurred after a myeloablative conditioning regimen, the IPS and bronchiolitis obliterans syndrome cases occurred after a reduced-intensity conditioning regimen. In the placebo group, a case of bronchiolitis obliterans syndrome in a patient conditioned with a myeloablative regimen was diagnosed on Day 311 after randomization. When all data from the first year after randomization were considered, the risk of developing a noninfectious complication remained lower among BDP-treated patients, but this did not reach statistical significance (HR=0.70, 95% confidence interval [CI]0.19-2.57, p=0.58). The overall risk of developing a pulmonary infection by one year was lower for the BDP group, although this was not statistically significant (HR=0.67 (0.27-1.66, p=0.38)).

Figure 1:
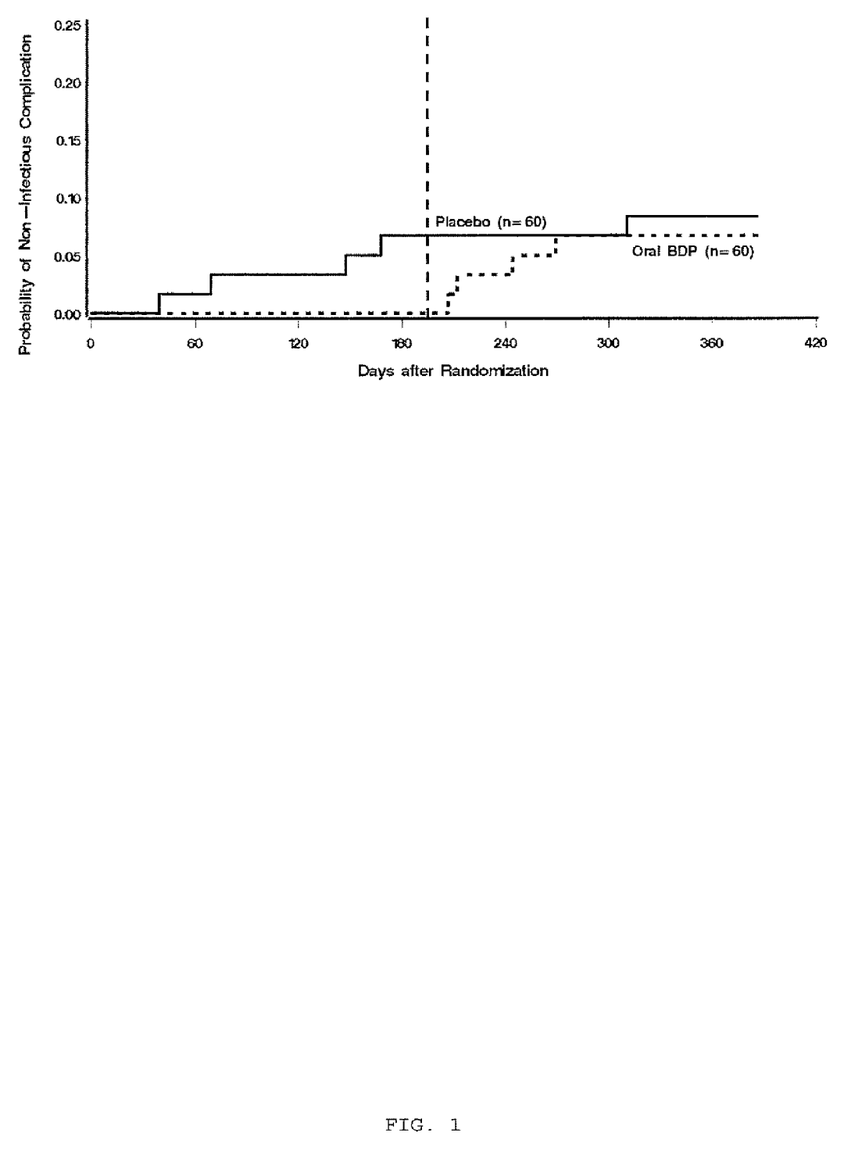
FIG. 1 depicts cumulative incidence of non-infectious pulmonary complications after treatment randomization. Vertical dashed line indicates Day 200 after treatment randomization. Prior to Day 200 after treatment randomization, no cases of non-infectious pulmonary complications occurred among the BDP-treated patients.

Among 60 placebo-treated patients, four noninfectious complications occurred within the first 200 days after randomization (FIG. 1). These cases were COP/BOOP (Day 39) and IPS (Day 69, 148, 168). All of these cases occurred after a myeloablative conditioning regimen. Among 60 BDP-treated patients, there were no cases of noninfectious pulmonary complications during the first 200 days after randomization (FIG. 1). When considered as a time-to-event endpoint, the risk of developing a noninfectious complication within the first 200 days after randomization was reduced among BDP-treated patients, (hazard ratio [HR]=0, p=0.04; p=0.06 with the exact log-rank test).

These data suggest that oral BDP may have a protective effect on early decline in pulmonary diffusing capacity, which commonly occurs by Day 80 after transplant because of interstitial lung injury. We hypothesize that preservation of diffusing capacity was due to delivery of the potent immunosuppressive metabolite 17-BMP to the lungs via GI mucosa, portal vein, and pulmonary artery.

Example II: Categorization of Pulmonary Disease after Hematopoietic Cell Transplantation While blinded to randomization assignment, investigators reviewed all patients' pulmonary radiologic records accumulated from the time of randomization to one year after transplantation. The medical records of all patients with abnormal pulmonary radiological findings were reviewed to determine whether the pulmonary disease was a clinically significant noninfectious or infectious syndrome. Clinically significant noninfectious pulmonary syndromes included idiopathic pneumonia syndrome (IPS), defined as widespread alveolar injury in the absence of active lower respiratory tract infection after HCT (Freudenberger T D et al., Blood, 2003; 102:3822-3828, diffuse alveolar hemorrhage (DAH), defined as IPS with bronchioalveolar lavage showing progressively bloodier return, or biopsy-proven cryptogenic organizing pneumonia (COP) otherwise known as bronchiolitis obliterans organizing pneumonia (BOOP). Clinically significant pulmonary infection required microbiologic documentation of an infectious agent in the respiratory tract via bronchoscopy or resolution of pulmonary abnormalities after empirical antibiotic therapy with no addition of immunosuppressive agents.

Figure 2:
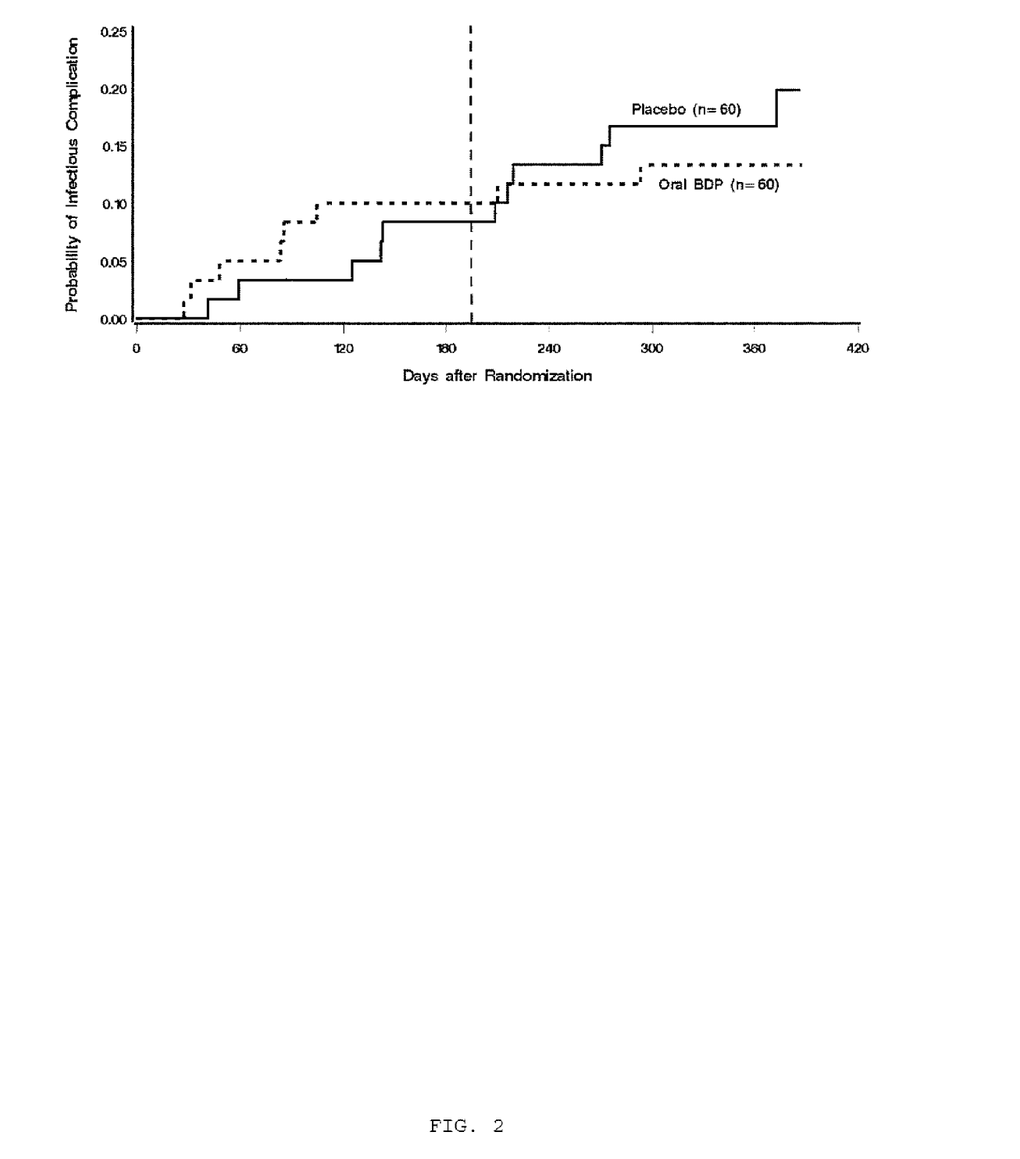
FIG. 2 depicts cumulative incidence of pulmonary infections after treatment randomization. Vertical dashed line indicates Day 200 after treatment randomization. There were no statistically significant differences in the risk of pulmonary infections between the two treatment groups at Day 200 or one year after randomization.

The causes of pulmonary infections are summarized in Table 3. Among 60 placebo-treated patients, 11 cases of pulmonary infection occurred after randomization during the first year, five (45%) of which occurred within the first 200 days after randomization (FIG. 2). Among 60 BDP-treated patients, 8 cases of pulmonary infection occurred during the first year after randomization, 6 (75%) of which occurred during the first 200 days after randomization (FIG. 2). When considered as a time-to-event endpoint, the risk of developing a pulmonary infection was not statistically significantly different between EDP and placebo (HR=1.21 (0.37-3.96, p=0.75)).

TABLE 3

Causes of pulmonary infection according to treatment group

| Placebo | | Oral BDP | |
|---|---|---|---|
| Cause of infection | Day post-randomization | Cause of infection | Day post-randomization |
| Fungal, nonspecific | 41 | Legionella spp. | 27 |
| Aspergillus fumigatus | 59 | Polymicrobial bacteria | 31 |
| Unknown cause | 125 | Pseudomonas aeruginosa | 48 |
| Aspergillus spp. | 142 | | |
| Unknown cause | 143 | Candida glabrata | 83 |
| Pneumocystis jiroveci | 209 | Unknown cause | 85 |
| Aspergillus spp. | 216 | Unknown cause | 104 |
| Unknown cause | 219 | Parainfluenza and | 210 |
| Aspergillus terreus | 270 | Aspergillus spp. | |
| Candida spp. | 275 | Klebsiella pneumoniae | 293 |
| Streptococcus hominis | 373 | | |

Example III: Measurement 17-Beclomethasone Monoproprionate (17-BMP) in Blood from the Right Atrium Four FHCRC patients enrolled in the Phase 3 randomized study had participated in a sub-analysis of BDP pharmacokinetics. At study Day 50, blood was drawn from the right atrium via an indwelling Hickman catheter at frequent intervals after a morning dose of oral BDP 2 mg (1 mg each in gastric-release and enteric-coated tablets). Blood samples were collected over EDTA, plasma was collected after centrifugation at 4° C., and aliquots were frozen at −20° C. until analysis for BDP and 17-BMP using high-pressure liquid chromatography and mass spectroscopy (MDS Pharma Services, Montreal, Canada). Pharmacokinetic parameters were calculated using WinNonlin v. 2.1 (Pharsight Corp, Palo Alto Calif.). Plasma concentration-time data were plotted and non-compartmental parameters were calculated using the linear trapezoidal rule. Estimates for half-lives were obtained using regression analysis by specifying an appropriate range of time points for the most linear portions of the log concentration-linear time data.

Peak concentrations of 17-BMP in right atrial blood were achieved at a median of 1.5 hours after oral dosing of BDP 2 mg on the morning of study Day 50. The median Cm was 1738 pg/mL (range 632-3701). Median steady state exposure to 17-BMP was 5347 pg·hr/mL (range 3273-5201) as estimated by $AUC_{0-4\ hr}$. The median half-life of 17-BMP was 6.3 hours (range 3.1-6.8). No BDP was detected in right atrial blood.

What is claimed is:

1. A method of treating an interstitial lung disease comprising oral delivery of an effective amount of a topical active corticosteroid, wherein the corticosteroid is beclomethasone dipropionate, sufficient to expose a metabolite thereof, wherein the metabolite is 17-beclomethasone monopropionate, to the pulmonary circulation of a subject.

2. The method of claim 1, wherein the effective amount of the topical active corticosteroid is at least 8 mg/day.

3. The method of claim 1, wherein the interstitial lung disease includes at least one member of the group consisting of idiopathic pulmonary fibrosis, nonspecific interstitial pneumonitis, bronchiolitis obliterans with organizing pneumonia, respiratory bronchiolitis-associated interstitial lung disease, desquamative interstitial pneumonitis, lymphocytic interstitial pneumonitis, acute interstitial pneumonitis and bronchopulmonary dysplasia.

4. A method of delivering a corticosteroid or metabolite thereof to a subject's pulmonary artery for treatment of an interstitial lung disease by administering to the subject an effective amount of an oral dosage of the corticosteroid, wherein the corticosteroid is beclomethasone dipropionate or its metabolite 17-beclomethasone monopropionate.

5. The method of claim 4, wherein the effective amount of the topical active corticosteroid is at least 8 mg/day.

6. The method of claim 4, wherein the interstitial lung disease includes at least one member of the group consisting of idiopathic pulmonary fibrosis, nonspecific interstitial pneumonitis, bronchiolitis obliterans with organizing pneumonia, respiratory bronchiolitis-associated interstitial lung disease, desquamative interstitial pneumonitis, lymphocytic interstitial pneumonitis, acute interstitial pneumonitis and bronchopulmonary dysplasia.

7. A method for preventing, ameliorating and/or treating damage resulting from an interstitial lung disease, the method comprising delivering to a subject's pulmonary artery a metabolite of an orally administered corticosteroid in a dose that is at least 5 fold greater than the corticosteroid delivered via inhalation, wherein the corticosteroid is beclomethasone dipropionate and the metabolite is 17-beclomethasone monopropionate.

8. The method of claim 7, wherein the effective amount of the topical active corticosteroid is at least 8 mg/day.

9. The method of claim 7, wherein the interstitial lung disease includes at least one member of the group consisting of idiopathic pulmonary fibrosis, nonspecific interstitial pneumonitis, bronchiolitis obliterans with organizing pneumonia, respiratory bronchiolitis-associated interstitial lung disease, desquamative interstitial pneumonitis, lymphocytic interstitial pneumonitis, acute interstitial pneumonitis and bronchopulmonary dysplasia.

* * * * *